United States Patent
Alamin et al.

(10) Patent No.: US 8,668,719 B2
(45) Date of Patent: Mar. 11, 2014

(54) METHODS AND APPARATUS FOR IMPROVING SHEAR LOADING CAPACITY OF A SPINAL SEGMENT

(75) Inventors: Todd Alamin, Woodside, CA (US); Louis Fielding, San Carlos, CA (US); Manish Kothari, San Rafael, CA (US)

(73) Assignee: Simpirica Spine, Inc., San Carlos, CA (US)

( * ) Notice: Subject to any disclaimer, the term of this patent is extended or adjusted under 35 U.S.C. 154(b) by 148 days.

(21) Appl. No.: 12/750,190

(22) Filed: Mar. 30, 2010

(65) Prior Publication Data
US 2010/0249839 A1 Sep. 30, 2010

Related U.S. Application Data

(60) Provisional application No. 61/164,768, filed on Mar. 30, 2009.

(51) Int. Cl.
*A61B 17/70* (2006.01)
*A61B 17/88* (2006.01)
(52) U.S. Cl.
USPC .............................. 606/248; 606/279; 606/263
(58) Field of Classification Search
USPC .................... 606/248–249, 257, 263, 279, 74
See application file for complete search history.

(56) References Cited

U.S. PATENT DOCUMENTS

| | | |
|---|---|---|
| 3,648,691 A | 3/1972 | Lumb et al. |
| 4,246,660 A | 1/1981 | Wevers |
| 4,643,178 A | 2/1987 | Nastari et al. |
| 4,708,132 A | 11/1987 | Silvestrini |
| 4,743,260 A | 5/1988 | Burton |
| 4,772,286 A | 9/1988 | Goble et al. |
| 4,776,851 A | 10/1988 | Bruchman et al. |
| 4,794,916 A | 1/1989 | Porterfield et al. |

(Continued)

FOREIGN PATENT DOCUMENTS

| | | |
|---|---|---|
| EP | 0 322 334 A1 | 6/1989 |
| EP | 0 743 045 A2 | 11/1996 |

(Continued)

OTHER PUBLICATIONS

International Search Report and Written Opinion of PCT Application No. PCT/US2010/029263, mailed May 25, 2010, 13 pages total.

(Continued)

*Primary Examiner* — Eduardo C Robert
*Assistant Examiner* — Julianna N Harvey
(74) *Attorney, Agent, or Firm* — Wilson Sonsini Goodrich & Rosati (57) ABSTRACT

A method for improving shear loading capacity of a spinal segment having a superior vertebra, an inferior vertebra or sacrum, and a facet joint, includes providing a constraint device having an upper portion, a lower portion and a compliance member coupled therebetween. The constraint device is coupled with the spinal segment such that the upper portion of the constraint device is coupled with the superior vertebra and the lower portion of the constraint device is coupled with the inferior vertebra or a sacrum. The constraint device provides a force resistant to flexion of the spinal segment. Also, length or tension in the constraint device is adjusted so as to increase engagement between an upper portion of the facet joint and a lower portion of the facet joint, thereby increasing capacity of the spinal segment to resist shear loading.

44 Claims, 10 Drawing Sheets

(56) References Cited

U.S. PATENT DOCUMENTS

| | | |
|---|---|---|
| 4,870,957 A | 10/1989 | Goble et al. |
| 4,955,910 A | 9/1990 | Bolesky |
| 4,966,600 A | 10/1990 | Songer et al. |
| 5,002,574 A | 3/1991 | May et al. |
| 5,011,484 A | 4/1991 | Breard |
| 5,092,866 A | 3/1992 | Breard et al. |
| 5,108,433 A | 4/1992 | May et al. |
| 5,116,340 A | 5/1992 | Songer et al. |
| 5,171,280 A | 12/1992 | Baumgartner |
| 5,180,393 A | 1/1993 | Commarmond |
| 5,282,863 A | 2/1994 | Burton |
| 5,354,917 A | 10/1994 | Sanderson et al. |
| 5,395,374 A | 3/1995 | Miller et al. |
| 5,415,658 A | 5/1995 | Killpela et al. |
| 5,415,661 A | 5/1995 | Holmes |
| 5,449,361 A | 9/1995 | Preissman |
| 5,456,722 A | 10/1995 | McLeod et al. |
| 5,458,601 A | 10/1995 | Young, Jr. et al. |
| 5,462,542 A | 10/1995 | Alesi, Jr. |
| 5,496,318 A | 3/1996 | Howland et al. |
| 5,540,698 A | 7/1996 | Preissman |
| 5,562,737 A | 10/1996 | Graf |
| 5,609,634 A | 3/1997 | Voydeville |
| 5,628,756 A | 5/1997 | Barker, Jr. et al. |
| 5,645,084 A * | 7/1997 | McKay ............... 128/898 |
| 5,645,599 A | 7/1997 | Samani |
| 5,669,917 A | 9/1997 | Sauer et al. |
| 5,672,175 A | 9/1997 | Martin |
| 5,707,379 A | 1/1998 | Fleenor et al. |
| 5,725,582 A | 3/1998 | Bevan et al. |
| 5,902,305 A | 5/1999 | Beger et al. |
| RE36,221 E | 6/1999 | Breard et al. |
| 5,928,232 A | 7/1999 | Howland et al. |
| 5,933,452 A | 8/1999 | Eun |
| 5,935,133 A | 8/1999 | Wagner et al. |
| 5,964,769 A | 10/1999 | Wagner et al. |
| 5,989,256 A | 11/1999 | Kuslich et al. |
| 6,053,921 A | 4/2000 | Wagner et al. |
| 6,193,721 B1 * | 2/2001 | Michelson ............... 606/70 |
| 6,224,630 B1 | 5/2001 | Bao et al. |
| 6,248,106 B1 | 6/2001 | Ferree |
| 6,283,996 B1 | 9/2001 | Chervitz et al. |
| 6,296,643 B1 | 10/2001 | Hopf et al. |
| 6,312,431 B1 | 11/2001 | Asfora |
| 6,322,279 B1 | 11/2001 | Yamamoto et al. |
| 6,364,883 B1 | 4/2002 | Santilli |
| 6,378,289 B1 | 4/2002 | Trudeau et al. |
| 6,391,030 B1 | 5/2002 | Wagner et al. |
| 6,395,018 B1 * | 5/2002 | Castaneda .............. 623/1.13 |
| 6,436,099 B1 | 8/2002 | Drewry et al. |
| 6,451,019 B1 | 9/2002 | Zucherman et al. |
| 6,468,309 B1 | 10/2002 | Lieberman |
| 6,517,578 B2 | 2/2003 | Hein |
| 6,558,389 B2 | 5/2003 | Clark et al. |
| 6,582,433 B2 * | 6/2003 | Yun ............................ 606/249 |
| 6,605,091 B1 | 8/2003 | Iwanski |
| 6,616,669 B2 | 9/2003 | Ogilvie et al. |
| 6,626,944 B1 | 9/2003 | Taylor |
| 6,629,975 B1 | 10/2003 | Kilpela et al. |
| 6,652,527 B2 | 11/2003 | Zucherman et al. |
| 6,652,585 B2 | 11/2003 | Lange |
| 6,656,185 B2 | 12/2003 | Gleason et al. |
| 6,669,729 B2 | 12/2003 | Chin |
| 6,682,533 B1 | 1/2004 | Dinsdale et al. |
| 6,689,140 B2 | 2/2004 | Cohen |
| 6,689,168 B2 | 2/2004 | Lieberman |
| 6,695,852 B2 | 2/2004 | Gleason |
| 6,712,819 B2 | 3/2004 | Zucherman et al. |
| 6,716,245 B2 | 4/2004 | Pasquet et al. |
| 6,761,720 B1 | 7/2004 | Senegas |
| 6,828,357 B1 | 12/2004 | Martin et al. |
| 6,835,205 B2 | 12/2004 | Atkinson et al. |
| 6,835,207 B2 | 12/2004 | Zacouto et al. |
| 6,899,716 B2 | 5/2005 | Cragg et al. |
| 6,946,000 B2 | 9/2005 | Senegas et al. |
| 7,029,475 B2 | 4/2006 | Panjabi |
| 7,087,083 B2 | 8/2006 | Pasquet et al. |
| 7,101,398 B2 | 9/2006 | Dooris et al. |
| 7,163,558 B2 | 1/2007 | Senegas et al. |
| 7,201,751 B2 | 4/2007 | Zucherman et al. |
| 7,238,204 B2 | 7/2007 | Le Couedic et al. |
| 7,413,576 B2 | 8/2008 | Sybert et al. |
| 7,445,637 B2 | 11/2008 | Taylor |
| 7,452,351 B2 | 11/2008 | Miller et al. |
| 7,458,981 B2 | 12/2008 | Fielding et al. |
| 7,520,887 B2 | 4/2009 | Maxy et al. |
| 7,524,324 B2 | 4/2009 | Winslow |
| 7,553,320 B2 | 6/2009 | Molz, IV et al. |
| 7,559,951 B2 | 7/2009 | Disilvestro et al. |
| 7,591,837 B2 | 9/2009 | Goldsmith |
| 7,608,094 B2 | 10/2009 | Falahee |
| 2002/0029039 A1 * | 3/2002 | Zucherman et al. ............ 606/61 |
| 2003/0088251 A1 | 5/2003 | Braun et al. |
| 2004/0116927 A1 | 6/2004 | Graf |
| 2004/0167520 A1 | 8/2004 | Zucherman et al. |
| 2004/0172132 A1 | 9/2004 | Ginn |
| 2005/0033435 A1 | 2/2005 | Belliard et al. |
| 2005/0049708 A1 | 3/2005 | Atkinson et al. |
| 2005/0123581 A1 | 6/2005 | Ringeisen et al. |
| 2005/0131405 A1 * | 6/2005 | Molz et al. ...................... 606/61 |
| 2005/0154390 A1 | 7/2005 | Biedermann et al. |
| 2005/0192581 A1 | 9/2005 | Molz et al. |
| 2005/0216017 A1 * | 9/2005 | Fielding et al. ................. 606/74 |
| 2005/0267470 A1 | 12/2005 | McBride |
| 2005/0267518 A1 | 12/2005 | Wright et al. |
| 2006/0036324 A1 | 2/2006 | Sachs et al. |
| 2006/0041259 A1 | 2/2006 | Paul et al. |
| 2006/0064166 A1 | 3/2006 | Zucherman et al. |
| 2006/0084976 A1 | 4/2006 | Borgstrom et al. |
| 2006/0106381 A1 | 5/2006 | Ferree et al. |
| 2006/0106397 A1 | 5/2006 | Lins |
| 2006/0136060 A1 | 6/2006 | Taylor |
| 2006/0142760 A1 | 6/2006 | McDonnell |
| 2006/0149230 A1 | 7/2006 | Kwak et al. |
| 2006/0195102 A1 | 8/2006 | Malandain |
| 2006/0217726 A1 | 9/2006 | Maxy et al. |
| 2006/0240533 A1 | 10/2006 | Sengupta et al. |
| 2006/0241610 A1 | 10/2006 | Lim et al. |
| 2006/0271055 A1 | 11/2006 | Thramann |
| 2007/0010822 A1 | 1/2007 | Zalenski et al. |
| 2007/0073293 A1 | 3/2007 | Martz et al. |
| 2007/0083200 A1 | 4/2007 | Gittings et al. |
| 2007/0213829 A1 | 9/2007 | Le Couedic et al. |
| 2007/0233096 A1 | 10/2007 | Garcia-Bengochea |
| 2007/0270828 A1 | 11/2007 | Bruneau et al. |
| 2007/0299445 A1 | 12/2007 | Shadduck et al. |
| 2008/0009866 A1 | 1/2008 | Alamin et al. |
| 2008/0021466 A1 | 1/2008 | Shadduck et al. |
| 2008/0027435 A1 | 1/2008 | Zucherman et al. |
| 2008/0033552 A1 | 2/2008 | Lee et al. |
| 2008/0045949 A1 * | 2/2008 | Hunt et al. ...................... 606/61 |
| 2008/0051784 A1 | 2/2008 | Gollogly |
| 2008/0097431 A1 | 4/2008 | Vessa |
| 2008/0108993 A1 * | 5/2008 | Bennett et al. .................. 606/61 |
| 2008/0114357 A1 | 5/2008 | Allard et al. |
| 2008/0125780 A1 | 5/2008 | Ferree |
| 2008/0177264 A1 | 7/2008 | Alamin et al. |
| 2008/0177298 A1 | 7/2008 | Zucherman et al. |
| 2008/0183209 A1 | 7/2008 | Robinson et al. |
| 2008/0262549 A1 | 10/2008 | Bennett et al. |
| 2008/0281423 A1 | 11/2008 | Sheffer et al. |
| 2008/0312693 A1 | 12/2008 | Trautwein et al. |
| 2008/0319487 A1 | 12/2008 | Fielding et al. |
| 2009/0030457 A1 | 1/2009 | Janowski et al. |
| 2009/0082820 A1 | 3/2009 | Fielding et al. |
| 2009/0118766 A1 | 5/2009 | Park et al. |
| 2009/0198282 A1 | 8/2009 | Fielding et al. |
| 2009/0264929 A1 | 10/2009 | Alamin et al. |
| 2009/0264932 A1 | 10/2009 | Alamin et al. |
| 2009/0270918 A1 | 10/2009 | Attia et al. |
| 2010/0004701 A1 | 1/2010 | Malandain et al. |
| 2010/0023060 A1 | 1/2010 | Bennett et al. |

(56) References Cited

U.S. PATENT DOCUMENTS

| | | |
|---|---|---|
| 2010/0036424 A1 | 2/2010 | Fielding et al. |
| 2010/0234890 A1 | 9/2010 | Alamin et al. |
| 2010/0234894 A1 | 9/2010 | Alamin et al. |

FOREIGN PATENT DOCUMENTS

| | | |
|---|---|---|
| EP | 0743045 A3 | 12/1996 |
| EP | 1 994 901 A1 | 11/2008 |
| FR | 2 681 525 A1 | 3/1993 |
| FR | 2 714 591 | 7/1995 |
| FR | 2 717 675 A1 | 9/1995 |
| FR | 2 828 398 A1 | 2/2003 |
| FR | 2 851 154 | 8/2004 |
| FR | 2 874 167 A1 | 2/2006 |
| FR | 2 884 136 A1 | 10/2006 |
| WO | WO 01/28442 | 4/2001 |
| WO | WO 02/03882 A2 | 1/2002 |
| WO | WO 02/03882 A3 | 5/2002 |
| WO | WO 02/051326 | 7/2002 |
| WO | WO 02/071960 | 9/2002 |
| WO | WO 03/045262 | 6/2003 |
| WO | WO 03/045262 A3 | 1/2004 |
| WO | WO 2004/052246 | 6/2004 |
| WO | WO 2004/073532 | 9/2004 |
| WO | WO 2004/073533 | 9/2004 |
| WO | WO 2005/110258 A1 | 11/2005 |
| WO | WO 2008/051423 | 5/2008 |
| WO | WO 2008/051801 | 5/2008 |
| WO | WO 2008/051802 | 5/2008 |
| WO | WO 2008/051806 | 5/2008 |
| WO | WO 2008/051802 A3 | 7/2008 |
| WO | WO 2008/051806 A3 | 7/2008 |
| WO | WO 2008/051801 A3 | 8/2008 |
| WO | WO 2009/149407 | 12/2009 |
| WO | WO 2010/028165 | 3/2010 |
| WO | WO 2010/028165 A8 | 10/2010 |
| WO | WO 2009/149407 A9 | 2/2011 |

OTHER PUBLICATIONS

Abbott Spine, Wallis Surgical Technique [Product Brochure], 2006; 24 pages total.

Al Baz et al., "Modified Technique of Tension Band Wiring in Flexion Injuries of the Middle and Lower Cervical Spine," Spine, vol. 20, No. 11, 1995, p. 1241-1244.

Chapter 11: Mechanical Aspects of Lumbar Spine in Musculoskeletal Biomechanics., Paul Brinckmann, Wolfgang Frobin, Gunnar Leivseth (Eds.), Georg Thieme Verlag, Stuttgart, 2002; p. 105-128.

Dickman et al., "Comparative Mechanical Properties of Spinal Cable and Wire Fixation Systems," Spine, vol. 22, No. 6, Mar. 15, 1997, pp. 596-604.

Frymoyer et al., "An Overview of the Incidence and Costs of Low Back Pain" Orthrop. Clin. North Am., 1991;22: 263-271.

Garner et al., "Development and Preclinical Testing of a New Tension-Band Device for the Spine: the Loop system," European Spine Journal, vol. 11 (Suppl 2), 2002 , pp. S186-S191.

Heller, "Stability of Different Wiring Techniques in Segmental Spinal Instrumentation. An Experimental Study," Archives of Orthopedic and Trauma Surgery, vol. 117, No. 1-2, Nov. 1997, pp. 96-99.

Leahy et al., "Design of Spinous Process Hooks for Flexible Fixation of the Lumbar Spine," Proceedings of the Institution of Mechanical Engineers, Part H, Journal of Engineering in Medicine, vol. 214, No. 5, Sep. 27, 2000 , pp. 479-487.

Leahy et al., "Mechanical Testing of a Flexible Fixation Device for the Lumbar Spine," Proceedings of the Institution of Mechanical Engineers, Part H: Journal of Engineering in Medicine, vol. 214, No. 5, Sep. 27, 2000 , pp. 489-495.

Medtronic Sofamor Danek USA, Inc., DIAM™ System Implant; 2006 [Product Brochure]; downloaded from the Internet: <http://spineinfo.ru/~files/DIAMST.pdf>, 20 pages total.

Minns et al., "Preliminary Design and Experimental Studies of a Novel Soft Implant for Correcting Sagittal Plane Instability in the Lumbar Spine," Spine, vol. 22, No. 16, Aug. 15, 1997, pp. 1819-1825.

Miyasaka et al., "Radiographic Analysis of Lumbar Motion in Relation to Lumbosacral Stability: Investigation of Moderate and Maximum Motion," Spine, vol. 25, No. 6, Mar. 15, 2000, pp. 732-737.

Papp et al., "An In Vitro Study of the Biomechanical Effects of Flexible Stabilization on the Lumbar Spine," Spine, vol. 22, No. 2, Jan. 15, 1997, pp. 151-155.

Shepherd et al., "Spinous Process Strength," Spine, vol. 25, No. 3, Feb. 1, 2000, pp. 319-323.

Shepherd, "Slippage of a Spinous Process Hook During Flexion in a Flexible Fixation System for the Lumbar Spine," Medical Engineering and Physics, vol. 23, No. 2, Mar. 2001, pp. 135-141.

Voydeville et al., "Ligamentoplastie Intervertebrale Avec Cale Souple dans Les Instabilities Lombaries" <<Intervertebral Ligamentoplasty with Flexible Wedge in Lumbar Instability,>>, Orthop Traumatol, vol. 2, 1992, pp. 259-264.

* cited by examiner

METHODS AND APPARATUS FOR IMPROVING SHEAR LOADING CAPACITY OF A SPINAL SEGMENT

CROSS-REFERENCES TO RELATED APPLICATIONS

The present application is a non-provisional of, and claims the benefit of U.S. Provisional Patent Application No. 61/164,768, the entire contents of which are incorporated herein by reference.

BACKGROUND OF THE INVENTION

1. Field of the Invention

The present invention relates generally to medical methods and apparatus. More particularly, the present invention relates to methods and apparatus used to improve shear loading capacity of a spinal segment. The methods and apparatus disclosed herein may be used alone or in combination with other orthopedic procedures intended to treat patients with spinal disorders such as degenerative spondylolisthesis.

A source of chronic low back pain is degenerative spondylolisthesis (DS). Degenerative Spondylolisthesis is a common clinical condition that typically presents in the 5th to 8th decades. The listhesis, or anterior translation of the superior vertebra relative to the inferior vertebra, is associated with degenerative changes which make the facet joints less resistant to shear forces seen by the segment.

As the center of mass of the human body is almost always in front of the spine, there is typically a net shear force exerted transversely across segments of the lower lumbar spine during activities of daily living. Each motion segment of the spine includes a disc and two facet joints (a left and a right facet joint) which share shear loads. As the facet joints degenerate, their typical coronal orientation becomes more sagittal, particularly in the superior section of the facet joint, further away from the pedicle. The facet joints' resistance to shear decreases as they become more sagittally oriented, and thus a larger share of the shear load is borne by the disc. The typical finding on flexion/extension films in patients with degenerative spondylolisthesis is that the amount of anterior translation increases when the segment is in flexion, and decreases when the segment is in extension. In the extended position, more of the facet joint is engaged, and thus the overall resistance to shear is increased.

Patients with DS typically present with symptoms of stenosis, and these symptoms can be addressed surgically with a decompression/laminectomy and fusion. Unfortunately, however, while decompression relieves pressure from nerves that cause pain, the removal of tissue involved in the decompression can also increase the flexion instability seen in DS, and, over time, the listhesis can increase and cause symptoms to recur. Because of the risk that a stand-alone decompression will increase post-operative instability, the standard of care in the United States is to treat degenerative spondylolisthesis patients with a decompression to address the presenting symptoms and a fusion to prevent progression of the instability and recurrence of symptoms. A surgeon performs decompression to relieve pressure on the nerve roots, typically at L4-L5, L3-L4, L5-S1, or elsewhere along the lumbar region of the spine. Bone is removed as required in order to provide pain relief, while still leaving some pieces of the bony structure intact. Less invasive techniques emphasize resection of only tissues causing neurological injury, and maintaining natural anatomy as much as possible. Often the superior portion of the superior spinous process in the affected spinal segment is left intact along with inferior portion of the inferior spinous process of the spinal segment. Additionally, a significant portion of the lamina will also be left intact.

Sometimes fusion and decompression are performed without instrumentation. Non-instrumented fusions typically require the post-operative use of a lumbar brace for 3-6 months to ensure that the fusion has the best chance to heal. Even with the brace, the non-union rate still can be as high as about 40-50%. Bracing is not particularly effective in limiting segmental motion, is expensive and irritating for patients and is associated with morbidities such as skin pressure sores.

Therefore, fusion often includes instrumentation of the affected spinal segment including the use of pedicle screws and stabilization rods that have high morbidity and complication rates. For example, because shear loading is transferred from the pedicle screws to the stabilization rod at their interface, sites of fatigue result, which can lead to instrumentation failure.

It would therefore be desirable to provide improved devices and methods that are simpler, less invasive and easier to use than existing treatment options that require fusion, rigid instrumentation and decompression procedures. Furthermore, it would be desirable for such improved devices and methods to reduce or eliminate anterior translation of the superior vertebra relative to the inferior vertebra. It would also be desirable for these devices and methods to increase the ability of the spinal segment to bear shear loads. It would also be desirable to have devices and methods able to withstand loading along the spinal segment with lower failure rates than traditional instrumentation. Such methods and devices also should be cost effective and manufacturable. Some or all of these objectives will be met by the devices and methods disclosed herein.

2. Description of the Background Art

U.S. Patent Publication No. 2005/0216017A1 now U.S. Pat. No. 7,458,981 is described below. Other patents and published applications of interest include: U.S. Pat. Nos. 4,966,600; 5,011,494; 5,092,866; 5,116,340; 5,282,863; 5,395,374; 5,415,658; 5,415,661; 5,449,361; 5,456,722; 5,462,542; 5,496,318; 5,540,698; 5,609,634; 5,645,599; 5,725,582; 5,902,305; Re. 36,221; U.S. Pat. Nos. 5,928,232; 5,935,133; 5,964,769; 5,989,256; 6,053,921; 6,312,431; 6,364,883; 6,378,289; 6,391,030; 6,468,309; 6,436,099; 6,451,019; 6,582,433; 6,605,091; 6,626,944; 6,629,975; 6,652,527; 6,652,585; 6,656,185; 6,669,729; 6,682,533; 6,689,140; 6,712,819; 6,689,168; 6,695,852; 6,716,245; 6,761,720; 6,835,205; Published U.S. Patent Application Nos. 2002/0151978; 2004/0024458; 2004/0106995; 2004/0116927; 2004/0117017; 2004/0127989; 2004/0172132; 2005/0033435; 2005/0049708; 2006/0069447; Published PCT Application Nos. WO 01/28442 A1; WO 02/03882 A2; WO 02/051326 A1; WO 02/071960 A1; WO 03/045262 A1; WO 2004/052246 A1; WO 2004/073532 A1; and Published Foreign Application Nos. EP 0322334 A1; and FR 2 681 525 A1.

BRIEF SUMMARY OF THE INVENTION

The present invention generally relates to medical methods and apparatus. More particularly, the present invention relates to methods and apparatus used to improve shear loading capacity of a spinal segment. The methods and apparatus disclosed herein may be used alone or in combination with other orthopedic procedures intended to treat patients with spinal disorders such as degenerative spondylolisthesis.

In a first aspect of the present invention, a spinal segment has a superior vertebra, an inferior vertebra or sacrum, and a left and a right facet joint therebetween. A method for improving shear loading capacity of the spinal segment comprises providing a constraint device having an upper portion, a lower portion and a compliance member coupled therebetween. The constraint device is coupled with the spinal segment such that the upper portion is coupled with the superior vertebra and the lower portion is coupled with the inferior vertebra or a sacrum. The constraint device provides a force resistant to flexion of the spinal segment. The method also includes the step of adjusting length or tension in the constraint device in order to increase engagement between an upper portion of the facet joint and a lower portion of the facet joint which increases the capacity of the spinal segment to resist segmental shear loading.

The upper portion of the constraint device may comprise an upper tether structure and the lower portion of the constraint device may comprise a lower tether structure. The compliance member may comprise a coil spring.

The constraint device may be coupled with the spinal segment using minimally invasive procedures. The upper portion of the constraint device may be disposed at least partially around a superior surface of, or through a superior spinous process and the lower portion of the constraint device may be disposed at least partially around an inferior surface of, or through an inferior spinous process. In some embodiments, the lower portion of the constraint device may be coupled with the sacrum. The constraint device may provide a force that resists spreading apart of a superior spinous process relative to an inferior spinous process. The constraint device may be coupled with the spinal segment without substantially restricting extension, lateral bending, or axial rotation of the spinal segment.

Length or tension in the constraint device may be adjusted in order to increase engagement between the upper portion of the facet joint and the lower portion of the facet joint, including when the spinal segment is in flexion. The upper portion of the facet joint may comprise an inferior articular process of the superior vertebra and the lower portion of the facet joint may comprise a superior articular process of the inferior vertebra. Increasing engagement between the upper and lower portions of the facet joint may increase the shear-loading capacity of the spinal segment thereby increasing stability of the spinal segment and reducing translation or listhesis of the superior vertebra relative to the inferior vertebra when a shear load is applied to the spinal segment. Translation may be in the anterior direction. Tension may be adjusted while the spinal segment is in a neutral position or while the patient is in a peri-operative implantation position. Tension may be adjusted to about 10 to 50 Newtons. The length of the constraint device may be adjusted until the constraint device is taut when the spinal segment is in a neutral position. The length may also be adjusted so that the upper and lower portions of the facet joint maintain engagement with one another when the spinal segment is in flexion.

The method may further comprise evaluating the spinal segment. Evaluation may include evaluation of facet joint engagement, curvature of the spinal segment, and intervertebral angle of the superior vertebra relative to the inferior vertebra. Evaluation may also include performing anatomical measurements of the spinal segment or adjacent regions or evaluating stability of the spinal segment. The evaluation may be accomplished by fluoroscopically imaging the spinal segment, direct visualization, manual palpation or manipulation of the spinal segment or measuring the spinal segment with a measuring instrument such as calipers or a ruler which may be radiopaque. One or more radiographic images of the spinal segment may be provided while the spinal segment is in a plurality of spinal postures.

The method may also include reducing or eliminating further progression of degenerative spondylolisthesis in the spinal segment. Intervertebral translation of the superior vertebra relative to the inferior vertebra may be reduced or eliminated and sagittal alignment of the spinal segment may be maintained or improved. Also, narrowing of the spinal canal or lateral foramina in the spinal segment due to translation of the superior vertebra relative to the inferior vertebra may be reduced or eliminated. The method may include decompression of the spinal segment in order to relieve pressure on nerves passing through the spinal segment. The decompression step may comprise decompressing the spinal segment while preserving at least half of each of the spinous processes in the spinal segment, and without disrupting mechanical integrity of the facet joints. The method may prevent or minimize disengagement of the upper portion of the facet joint from the lower portion of the facet joint when the spinal segment is in flexion. Additionally, the method may reduce peak loading on the superior and inferior vertebrae during flexion of the spinal segment relative to peak loading experienced when the spinal segment is instrumented with pedicle screws or cerclage wiring. Peak loading may also be reduced at the interface between the constraint device and the vertebrae during flexion of the spinal segment, again particularly compared to more rigid systems or systems with rigid interconnections. Sometimes a constraint device may be used and a fusion procedure may be performed concomitantly on the spinal segment.

In another aspect of the present invention, a spinal segment has a superior vertebra, an inferior vertebra and a facet joint therebetween. A constraint device for improving shear loading capacity of the spinal segment comprises an upper tether structure adapted to be coupled with a superior spinous process on the superior vertebra. The constraint device also comprises a lower tether structure adapted to be coupled with an inferior spinous process on the inferior vertebra or a sacrum. A compliance member is disposed between the upper and the lower tether structures. Length or tension in the constraint device is adjustable such that the constraint device provides a force resistant to flexion of the spinal segment. Also, the constraint device is further adapted to increase engagement between the upper and lower portions of the facet joint, thereby increasing capacity of the facet joint to resist shear loading. The increased engagement may occur when the spinal segment is in flexion. The upper and lower tether structures may be substantially non-distensible and they may comprise elongate bands. The constraint device may also include a second compliance member that may be disposed between the upper and the lower tether structures. The upper and the lower tether structures may be flexible such that neither tether structure transmits complex loading to the compliance members. The compliance members may comprise coil springs and both compliance members may be arranged to lie on either side of the spinal segment midline. The constraint device may be adapted to couple with the spinal segment without substantially restricting extension, lateral bending, or axial rotation of the spinal segment.

These and other embodiments are described in further detail in the following description related to the appended drawing figures.

DETAILED DESCRIPTION OF THE INVENTION

Figure 1A:
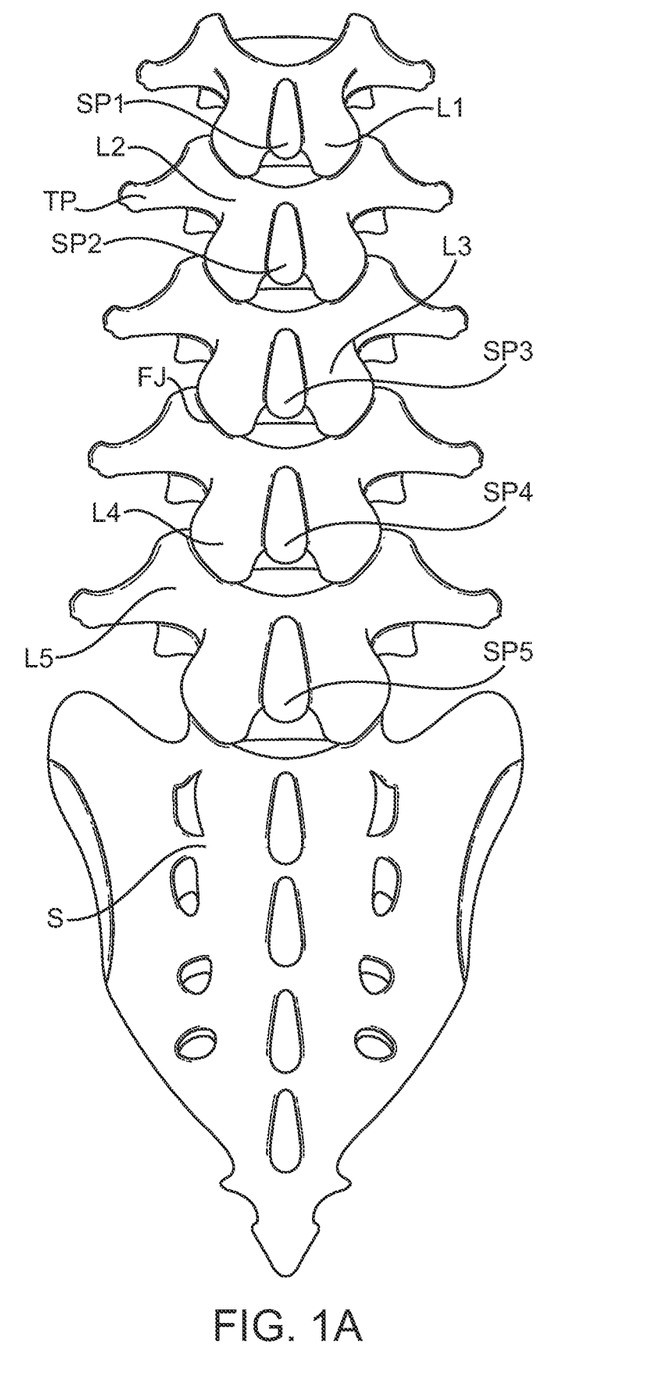
FIG. 1A is a schematic diagram illustrating the lumbar region of the spine.
Figure 1B:
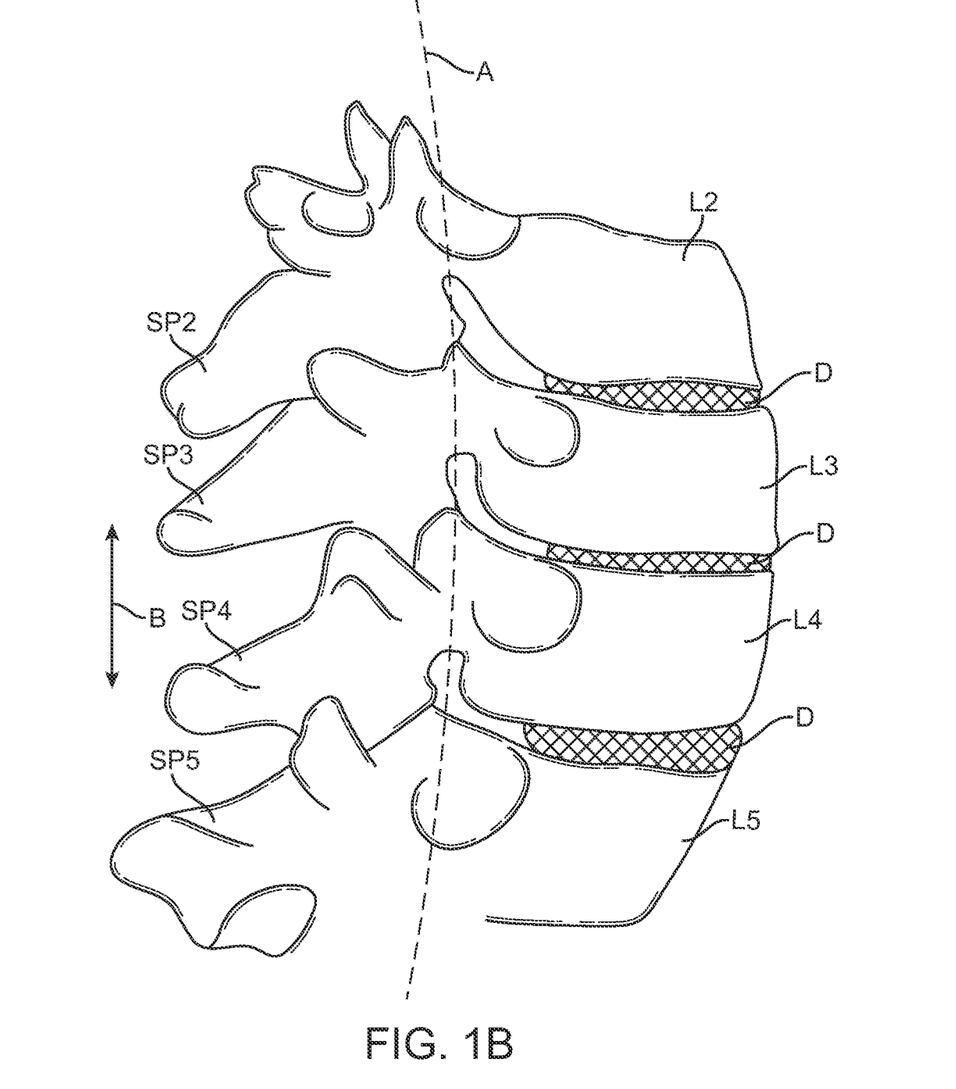
FIG. 1B a schematic illustration showing a portion of the lumbar region of the spine taken along a sagittal plane.

FIG. 1A is a schematic diagram illustrating the lumbar region of the spine including the spinous processes (SP), facet joints (FJ), lamina (L), transverse processes (TP), and sacrum (S). FIG. 1B is a schematic illustration showing a portion of the lumbar region of the spine taken along a sagittal plane and is useful for defining the terms "neutral position," "flexion," and "extension" that are often used in this disclosure.

As used herein, "neutral position" refers to the position in which the patient's spine rests in a relaxed standing position. The "neutral position" will vary from patient to patient. Usually, such a neutral position will be characterized by a slight curvature or lordosis of the lumbar spine where the spine has a slight anterior convexity and slight posterior concavity. In some cases, the presence of the constraint of the present invention may modify the neutral position, e.g. the device may apply an initial force which defines a "new" neutral position having some increased extension compared to the untreated spine. As such, the use of the term "neutral position" is to be taken in context of the presence or absence of the device. As used herein, "neutral position of the spinal segment" refers to the position of a spinal segment when the spine is in the neutral position.

Furthermore, as used herein, "flexion" refers to the motion between adjacent vertebrae of a spinal segment as the patient bends forward. Referring to FIG. 1B, as a patient bends forward from the neutral position of the spine, i.e. to the right relative to a curved axis A, the distance between individual vertebrae L on the anterior side decreases so that the anterior portion of the intervertebral disks D are compressed. In contrast, the individual spinous processes SP on the posterior side move apart in the direction indicated by arrow B. Flexion thus refers to the relative movement between adjacent vertebrae as the patient bends forward from the neutral position illustrated in FIG. 1B.

Additionally, as used herein, "extension" refers to the motion of the individual vertebrae L as the patient bends backward and the spine extends from the neutral position illustrated in FIG. 1B. As the patient bends backward, the anterior ends of the individual vertebrae will move apart. The individual spinous processes SP on adjacent vertebrae will move closer together in a direction opposite to that indicated by arrow B.

Figure 2A:
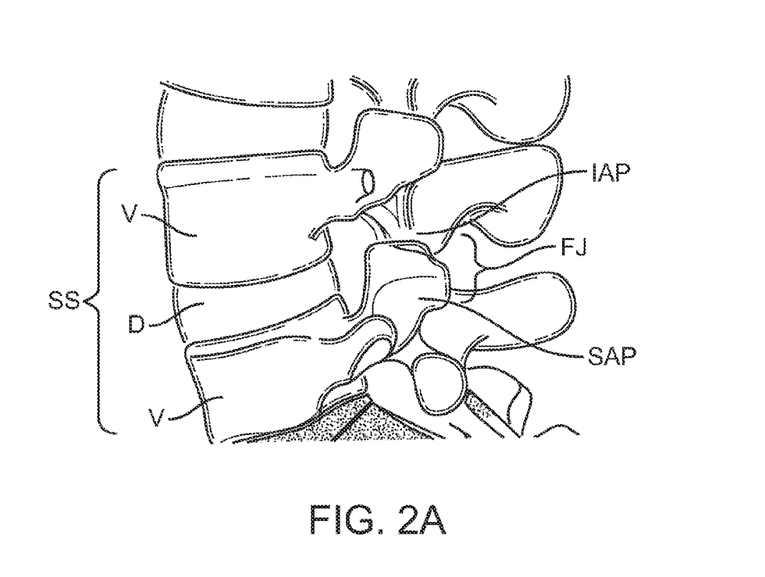
FIGS. 2A-2C illustrate various features of spinal vertebrae.
Figure 2B:
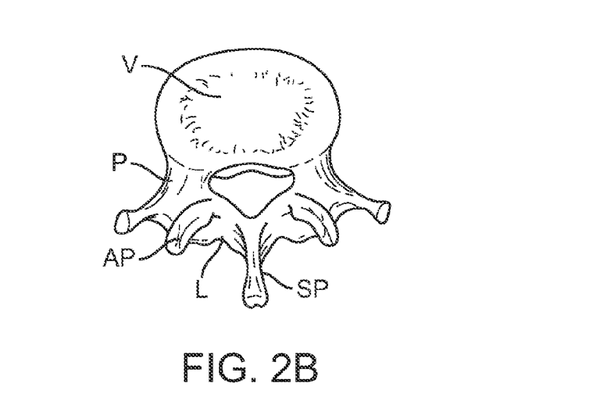
Figure 2C:
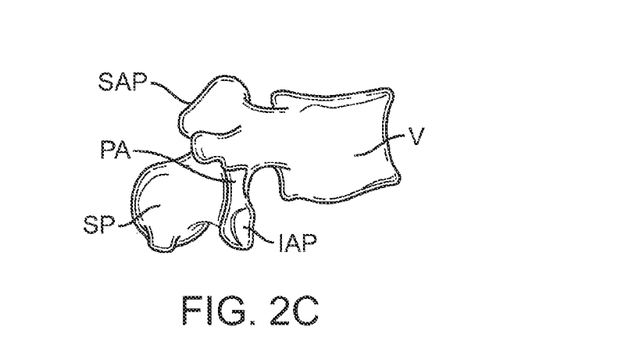

FIGS. 2A-2C illustrate various features and functions of spinal vertebrae. FIG. 2A illustrates a spinal motion segment SS which includes the intervertebral disc D surrounded by two adjacent vertebrae V and two facet joints FJ. A facet joint FJ is the interface between a superior articular process SAP of the inferior vertebra and the inferior articular process IAP of the superior vertebra. Facet joints are articular, synovial joints. Articular surfaces are cartilage. A fibrous joint capsule (capsular ligament) surrounds the joint. The orientation of the facet joint greatly affects the ranges of motion allowed at the motion segment. For example, the different orientations of the facet joints are the reason why the head can rotate relative to the neck by approximately 180 degrees, while the lumbar spine can only rotate a few degrees. FIG. 2B is an axial view of a vertebra V highlighting the pedicle P, articular process AP, lamina L, and spinous process SP. FIG. 2C is a sagittal view of a vertebra V highlighting the superior articular process SAP, the inferior articular process IAP, spinous process SP and the pars interarticularis PA.

Figure 3:
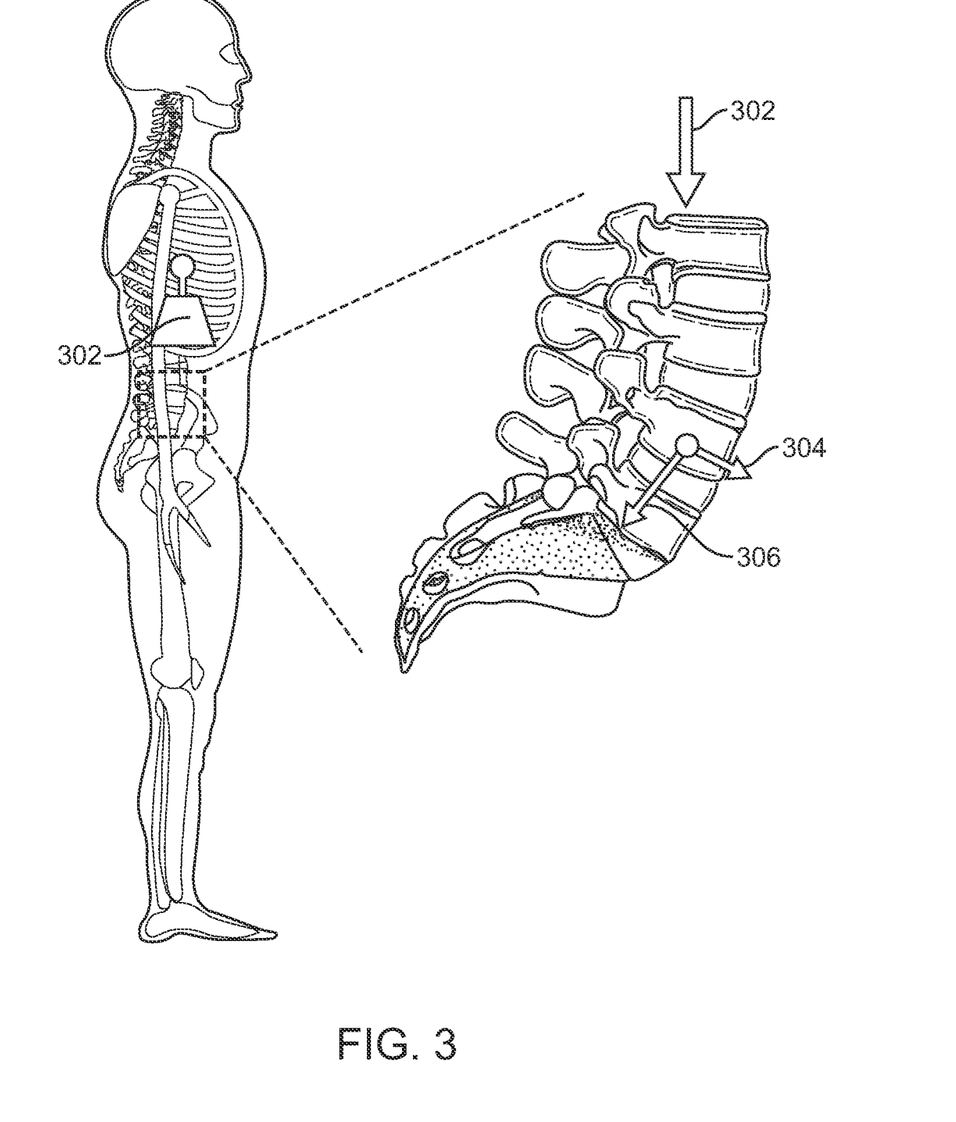
FIG. 3 illustrates loading on a spinal segment.

FIG. 3 illustrates loading in a spinal segment. In FIG. 3, the weight of the head and torso are represented by mass 302 which exerts a vertical load on the spinal segment. When the vertical load along the lumbar region of the spine is broken down into its components, resultant shear loading 304 in the anterior direction and axial loading 306 in the caudal direction both occur. Shear loading of the spinal segment is particularly prevalent in the lumbar region of the spine because of its curvature and orientation. Muscular forces such as from the psoas muscle may also impart significant shear loads. Shear loads may also further increase with other activities such as lifting or due to postural effects.

Figure 4A:
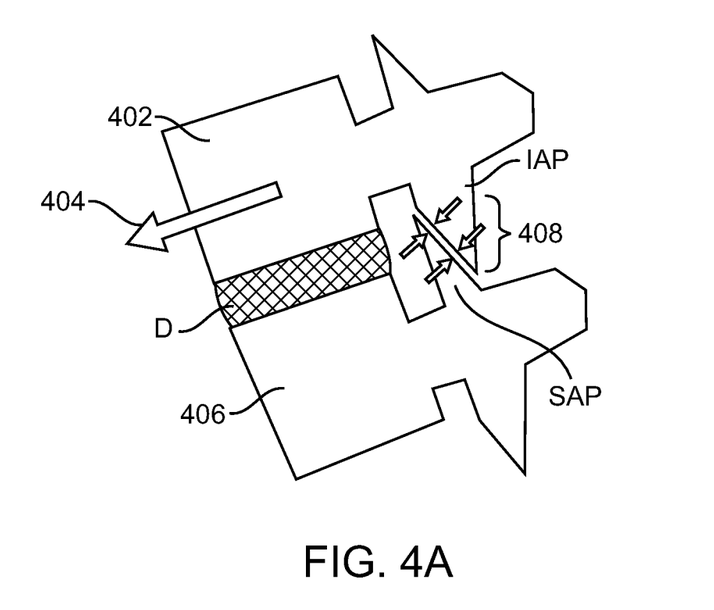
FIGS. 4A-4B illustrate how a normal spinal segment resists shear loading.
Figure 4B:
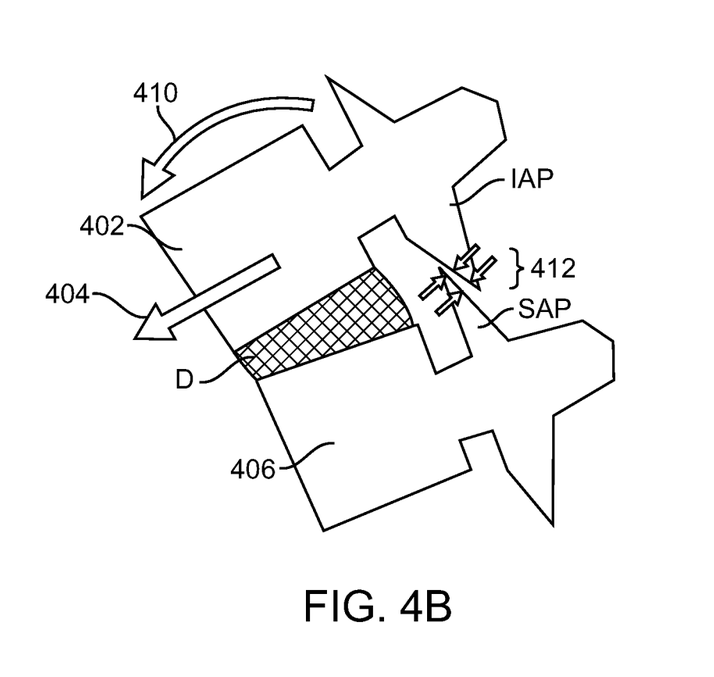

FIGS. 4A-4B illustrate how a healthy spinal segment resists shear loading. In FIG. 4A, a normal spinal motion segment includes a superior vertebra 402, an inferior vertebra 406 and the intervertebral disc D. The spinal segment also includes a left and right facet joint (only one visible in the lateral view of FIGS. 4A-4B). A facet joint is formed between the inferior articular process IAP of the superior vertebra 402 and the superior articular process SAP of the inferior vertebra 406. Shear loads are resisted by both the disc and facet joints. The shear load resisted by the facets is transferred through the contact area of the facets as projected onto the coronal plane. In FIG. 4A, when the spinal segment is in the neutral position and is subjected to an anterior directed shear force 404, the contact area 408 between the articular surfaces of the facet joint resist anterior translation of the superior vertebra relative to the inferior vertebra. FIG. 4B illustrates the spinal segment in flexion as indicated by arrow 410. As the motion segment moves into flexion (e.g. the patient bends forward), the facets slide across each other such that only the tips of the articular processes IAP, SAP are engaged 412. Degenerated facet joints may have less contact available between the articular processes, compared to a healthy facet joint with ample articular contact to resist shear loading.

Figure 5A:
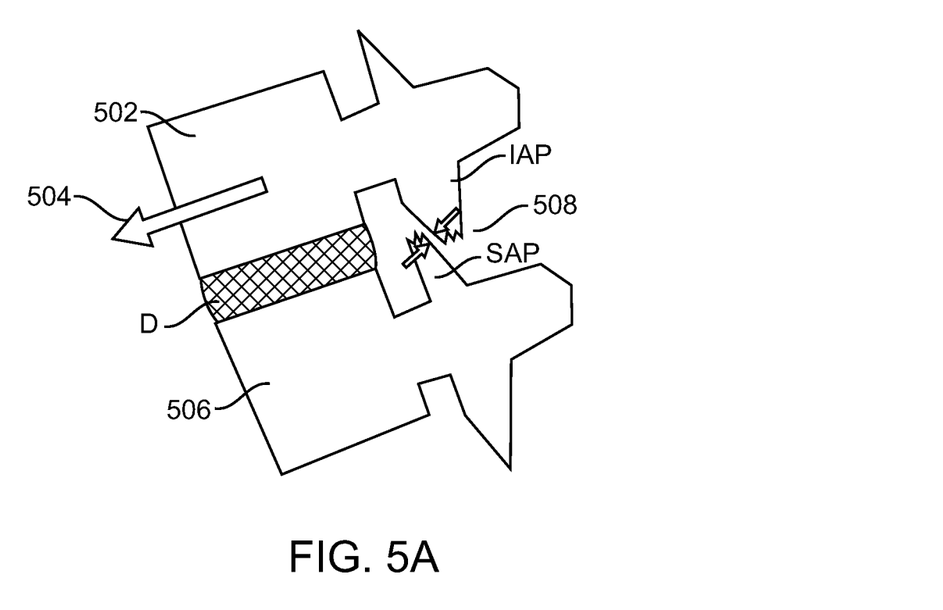
FIGS. 5A-5B illustrate how a degenerative facet joint reduces the ability of a spinal segment to resist shear loading.
Figure 5B:
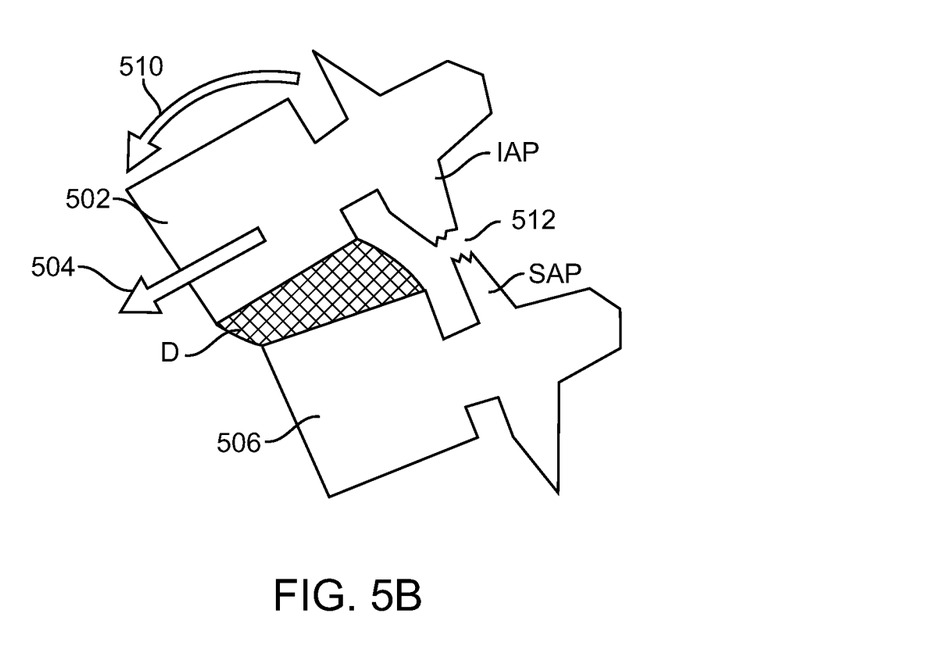
Figure 6A:
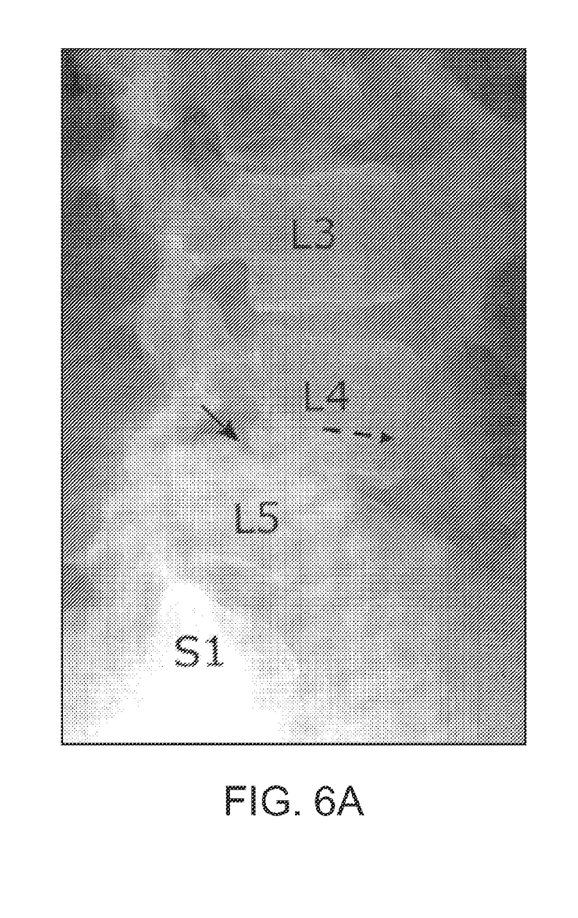
FIG. 6A illustrates an x-ray of degenerative spondylolisthesis in a spinal segment.
Figure 6B:
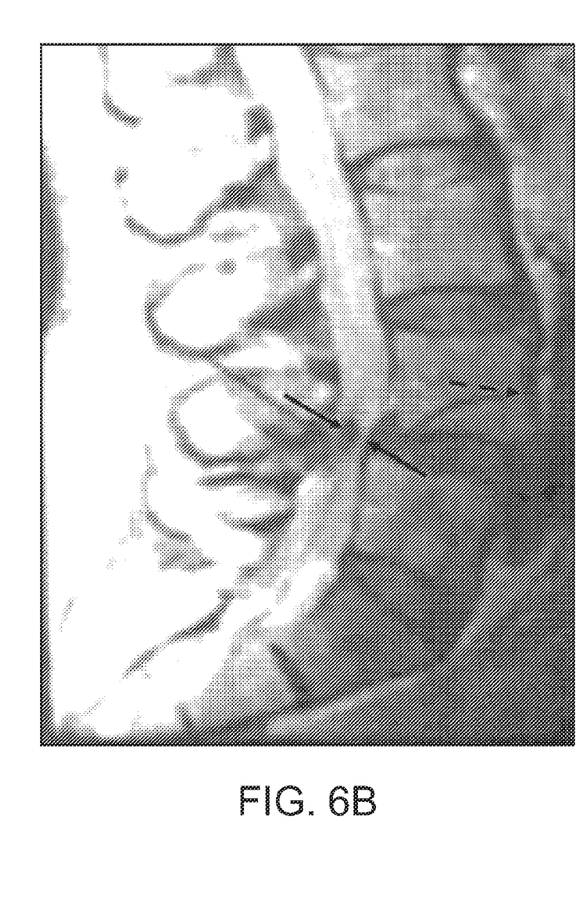
FIG. 6B illustrates an MRI of degenerative spondylolisthesis in a spinal segment.

FIGS. 5A-5B illustrate how a degenerative facet joint results in reduced resistance to shear loading in a spinal segment. In FIG. 5A, the spinal segment includes a superior vertebra 502, an inferior vertebra 506 and the intervertebral disc D. Like other articular joints, the facet joint may be subject to arthritic degeneration. In addition to causing primary pain in the joints, facet degeneration can lead to hypertrophy of the joints that may create neurological complications such as spinal stenosis, and may result in instability of the spinal motion segment. Degenerated facets may still be able to resist shear loading in postures when there is sufficient engagement of the articular surfaces. This often may be in postures of relative extension where the articular processes approximate as the spinal segment moves into extension. In FIG. 5A the articular processes IAP, SAP are degenerated as indicated symbolically by their jagged edges, yet the region of engagement 508 is still adequate enough in the neutral position or in extension to resist the shear loading from anterior directed shear force 504. FIG. 5B illustrates the motion segment of FIG. 5A in flexion, as indicated by arrow 510. When the spinal segment is in flexion, the articular processes IAP, SAP move away from one another and because of their degenerated states, IAP-SAP engagement is reduced or eliminated 512. Because the facet joint surfaces do not engage sufficiently, they do not sufficiently resist shear loading and the superior vertebra 502 translates forward in the anterior direction relative to the inferior vertebra 506. This condition is referred to as spondylolisthesis. When the condition is caused by degenerative changes as previously described, it is referred to as degenerative spondylolisthesis. Symptoms of degenerative spondylolisthesis can include back pain, leg pain, general pain, weakness and even neurologic injury due to effective narrowing of the spinal canal and foramina caused by the intervertebral translation. Spondylolisthesis is often accompanied by disc degeneration. Surgical decompression, where tissue is removed to relieve neural compression, may create additional segmental instability (particularly in flexion), and exacerbate the already reduced facet joint resistance to shear loading. FIG. 6A illustrates an x-ray and FIG. 6B illustrates an MRI of a spinal segment with degenerative spondylolisthesis at L4-L5 and resulting spinal cord compression. The vertebra experiencing translation is indicated by the dashed arrow and the neural compression is indicated by the solid arrow.

Figure 7:
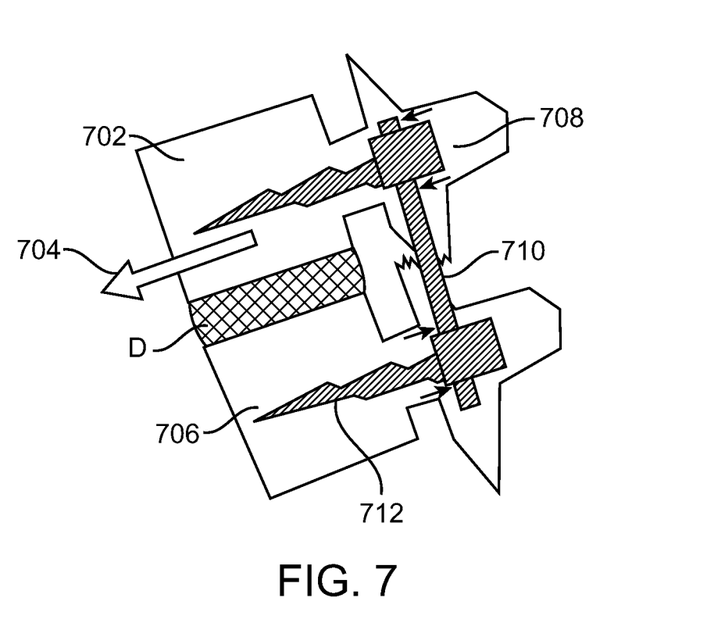
FIG. 7 illustrates a spinal segment instrumented with pedicle screws and a spinal rod.

Sometimes the affected spinal segment is instrumented with pedicle screws and stabilization rod systems in order to stabilize or correct the misalignment of adjacent vertebral bodies due to spondylolisthesis. This may also be accompanied by fusion and/or decompression. FIG. 7 illustrates an instrumented spinal segment. In FIG. 7, the spinal segment includes a superior vertebra 702, an inferior vertebra 706 and the intervertebral disc D. Pedicle screws 712 and a spinal rod 710 are coupled to the spinal segment in order to stabilize the motion segment and reduce or eliminate intervertebral translation. These rigid instrumentation systems along with even newer instrumentation systems that have flexible dynamic stabilization or motion preserving systems are still vulnerable to failure since, among other reasons, the shear load is transferred from the pedicle screw to the rod at their interface 708. This creates a site of fatigue and potential failure. Additionally, pedicle screw systems have known associated morbidities.

Figure 8:
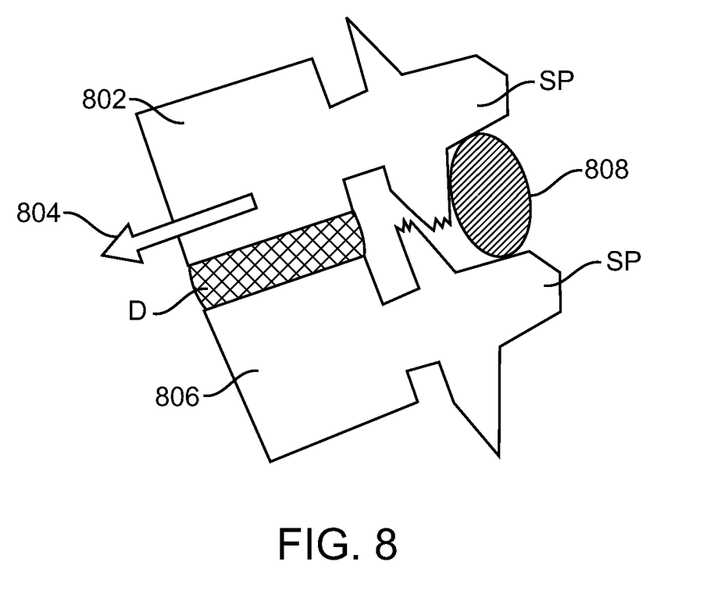
FIG. 8 illustrates an interspinous spacer implanted into a spinal segment.

In cases where the intervertebral translation results in neural compression, interspinous spacers are occasionally used as a treatment. The interspinous spacer distracts the posterior portions of adjacent spinous processes which may open the neural foramina and relieve neurological symptoms of stenosis commonly associated with spondylolisthesis. FIG. 8 illustrates the use of an interspinous spacer. In FIG. 8, a spinal motion segment includes a superior vertebrae 802, an inferior vertebra 806 and the intervertebral disc D. An interspinous spacer 808 is implanted between adjacent spinous processes SP in order to distract the processes. While this may alleviate neurological symptoms, these devices do not resist shear loading 804 or restore any flexion stability to the anatomy that may limit progression of the spondylolisthesis. In fact, distraction of the spinous processes may further decrease engagement of the facet joints, thus interspinous spacers may exacerbate such instability. Additionally, due to their placement between adjacent spinous processes, the interspinous spacers directly bear axial loads. Incidence of high peak loads during activities such as jumping or sitting down hard may transmit high loads through the implant and damage the posterior elements.

A system that restricts segmental flexion would maintain the spine in a posture where the facets are engaged to adequately resist shear loading. Implantation of a system consisting of straps coupled to a compliance member and looped around adjacent spinous processes will resist the spreading of the spinous processes apart from one another, thus restricting flexion of the motion segment. The compliance member allows for some motion and reduced peak loads on the spinous processes and posterior elements. The compliance member also helps reduce loads at the device interfaces, thereby reducing the risk of device failure. The ideal system will only restrict motion to a point where the facets maintain sufficient engagement, while allowing physiological motion below this range.

Figure 9:
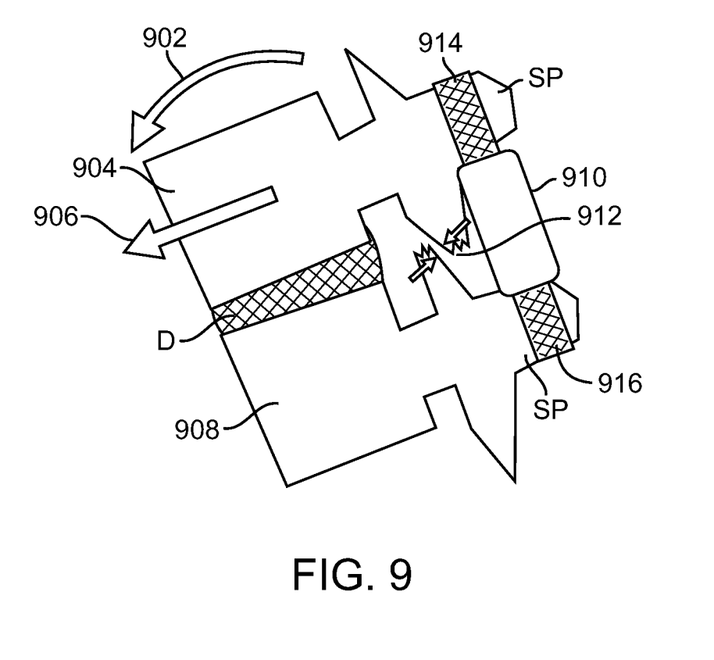
FIG. 9 illustrates the use of a system for restricting flexion in a spinal segment.

FIG. 9 illustrates the use of a system for restricting flexion in a spinal segment. In FIG. 9, the spinal segment includes a superior vertebra 904, the inferior vertebra 908 and the intervertebal disc D. A constraint device 910 is applied to the spinous processes SP of the superior and inferior vertebrae 904, 908. The constraint device restricts flexion 902 of the spinal segment by constraining distraction of the spinous processes SP, thereby increasing or maintaining engagement 912 of the facet joint and improving the capacity of the spinal segment to resist shear loading 906.

Use of the constraint device 910 may be alone or in combination with other procedures such as decompression (e.g. bone removal) to relieve pressure on the adjacent nerves. The constraint device includes an upper tether structure 914, a lower tether structure 916 and a compliance member 918. The upper tether structure 914 is disposed around or through a superior spinous process and the lower tether structure 916 is disposed around or through an inferior spinous process or coupled with the sacrum. Length or tension in the constraint device may be adjusted so that the constraint device provides the desired force resistant to flexion of the spinal segment. This may be accomplished by adjusting the length of the upper and/or lower tether structures 914, 916. Additionally, the compliance member 918 may be selected in order to adjust the elastic resistance of the constraint device 910. Preferably, two compliance members 918 are included in the constraint device 910, one on either side of the spinal segment midline (only one is visible in the side view of FIG. 9). The elastic resistance provided by the constraint device should be high enough to provide a force resistive to flexion that is also not excessive, since this could result in damage to the surrounding spinous processes. Additionally, the force should be high enough to prevent disengagement of the upper portion of the facet joint from the lower portion of the facet joint when the spinal segment is in flexion. The force should increase engagement of the facet joints during flexion (relative to the un-instrumented state), thereby increasing shear loading capacity of the facet joint and helping to stabilize the spinal segment. Compared to more rigid instrumentation systems such as pedicle screw constructs or cerclage wiring, the constraint device described herein also may reduce peak loading on the superior and inferior vertebrae during flexion and may also reduce peak loading at the interface between the constraint device and the vertebra during flexion. The constraint device may also reduce or eliminate translation or listhesis of the superior vertebra relative to the inferior vertebra, typically in the anterior direction. The constraint device may then reduce or eliminate further progression of spondylolisthesis in the spinal segment. Sagittal alignment of the spinal segment is therefore maintained or improved. Additionally, because intervertebral translation is reduced or eliminated, the narrowing of the spinal canal or lateral foramina may be reduced or eliminated. Additionally, unlike other rigid instrumentation systems (e.g. pedicle screws and rods) which constrain motion in the treated segment, constraint device 910 is flexible and therefore may be coupled with the spinal segment without substantially restricting extension, lateral bending, or axial rotation of the spinal segment.

Tension in the constraint device may be adjusted to any desired value, but often may be in the range from about 5 N to about 100 N, but more preferably may be in the range from about 10 N to about 30 N. Typically, the length of the constraint device or tension is adjusted while the patient is positioned perioperatively, such as the in prone position. According to surgeon preference, operative technique or concurrent procedures being performed, the patient may be positioned with the affected spinal segment in a neutral, flexion, or extension posture prior to device application. Device length may then be adjusted so that the constraint device is taut when the spinal segment is in the surgeon-adjusted position. The surgeon may also adjust length or tension in the constraint device such that the upper and lower portions of the facet joint maintain engagement with one another when the spinal segment is in flexion.

Once the constraint device has been applied to the spinal segment and adjusted, a surgeon often will evaluate the spinal segment to determine if the device has been properly implanted and adjusted. Often, the surgeon will evaluate engagement of the facet joint surfaces, examine spinal curvature, and review the sagittal angle formed by the endplates of the superior vertebra relative to the inferior vertebra. Other anatomical measurements of the spinal segment or adjacent areas may also be conducted as part of the evaluation process. For example, spinal stability may be examined. Often, the spinal segment will be evaluated using fluoroscopic images of the segment, or by direct visualization of the spine. Radiographic images of the spine in multiple postures, such as standing, seated, flexion and extension, may be particularly useful as part of the evaluation process. The spine may also be manually palpated, manipulated or a measuring instrument such as calipers or a radiopaque ruler may be used to measure the spine.

This procedure has a number of advantages over traditional methods for treating degenerative spondylolisthesis including a smaller incision and a less invasive dissection and surgical access. Also this procedure has less blood loss, requires less time and less anesthesia than decompression with fusion or facet joint replacement surgery. Additionally, in many cases no fusion is performed with this constraint device procedure, precluding autograft harvest and associated morbidity. But even in cases where fusion is performed, the constraint device may help the spinal segment to heal and fuse by constraining flexion and resisting shear. Also, pedicle screws are typically not required and therefore the patient has greater post-operative mobility and typically no risk of the complications and revisions associated with pedicle screws. Also, using a constraint device can obviate the need for a postoperative brace by more effectively controlling segmental motion in these patients without significantly adding to the required soft tissue dissection or the length of the surgery. The constraint device's elastic construction limits the strains exerted on the spinous processes, minimizing the risk of spinous process fracture, especially in elderly patients with poor bone quality. The device furthermore avoids the potential mid- to long-term morbidity associated with the typical violation of the adjacent facet joints associated with pedicle screw use, and may as such minimize the risk of subsequent adjacent level syndromes. Therefore, a constraint device having tether structures applied to an upper and a lower spinous process as previously described may provide a suitable internal construct that stabilizes the treated spinal segment. Thus an external brace may not be required, eliminating the challenges of using such a brace, including patient discomfort, patient compliance as well as cost. Additional details on the constraint device are disclosed below, as well as in U.S. Pat. No. 7,458,981 and U.S. Patent Publication No. 2008/0319487. Additional features on locking mechanisms that may be used to help adjust length or tension in the constraint device are disclosed in U.S. Patent Publication No. 2010/0023060 and International PCT Publication No. WO2009/149407. Additional methods and tools that may be used to couple the constraint device with the spinal segment are disclosed in U.S. Patent Publication Nos. 2008/0108993; 2008/0262549; and 2010/0004701. Furthermore, as discussed above, in some embodiments the constraint device may be coupled with the sacrum. Additional details on sacral attachment are disclosed in International PCT Application No. PCT/US2010/022767 and U.S. Patent Publication No. 2008/0009866. Each of the above listed references are hereby incorporated herein by reference in their entirety.

Figure 10:
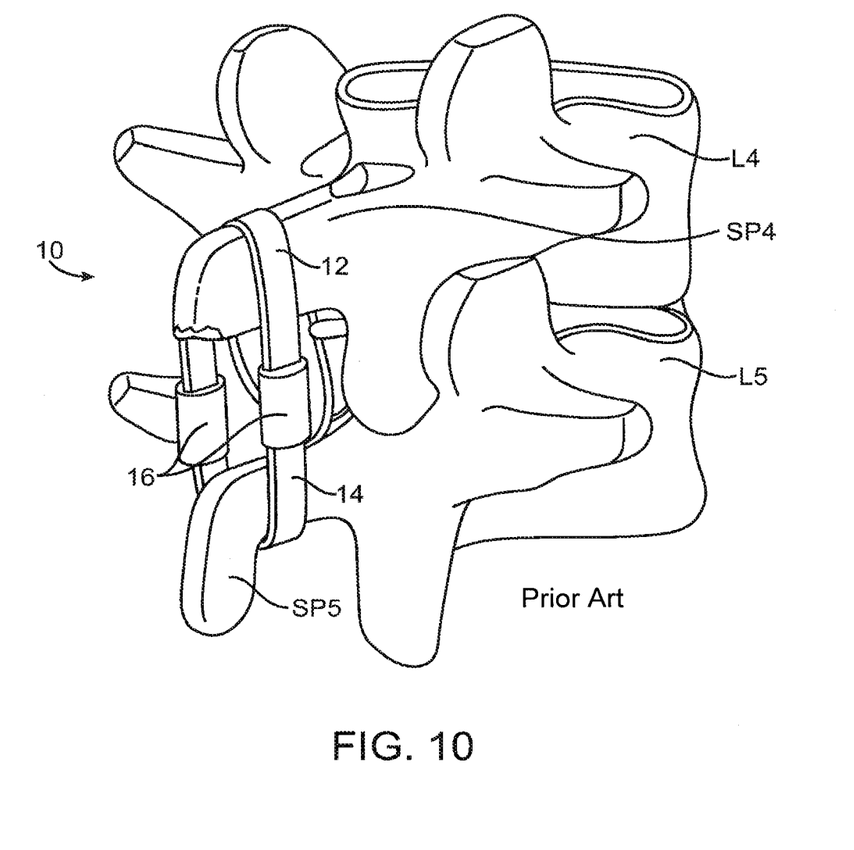
FIG. 10 illustrates a spinal implant of the type described in U.S. Pat. No. 7,458,981.

FIG. 10 more clearly illustrates the use of a constraint device attached to a spinal segment in order to increase shear loading capacity of the segment. In FIG. 10, an implant 10 typically comprises a tether structure having a flexible yet non-distensible upper strap component 12 and a flexible yet non-distensible lower strap component 14 joined by a pair of compliance members 16. The upper strap 12 is an elongate band shown disposed over the top of the spinous process SP4 of L4 while the lower strap 14 is also an elongate band shown extending over the bottom of the spinous process SP5 of L5. While the straps are non-distensible, they are flexible such that complex loading is not transmitted to the compliance members. The compliance member 16 will typically include an internal element, such as a spring or rubber block, which is attached to the straps 12 and 14 in such a way that the straps may be "elastically" or "compliantly" pulled apart as the spinous processes SP4 and SP5 move apart during flexion. In some embodiments, the compliance members may be coil springs. In this way, the implant provides an elastic tension on the spinous processes which is a force that resists flexion. The force increases as the processes move further apart. Usually, the straps themselves will be essentially non-compliant so that the degree of elasticity or compliance may be controlled and provided solely by the compliance members 16. The implant 10 may be applied to the spinal segment in a minimally invasive manner. Typically, a small puncture or gap is created in the interspinous ligament (not illustrated) superior to the superior spinous process and a second puncture or gap is created inferior to the inferior spinous process. The upper and lower straps may then be advanced through these fenestrations or gaps and the ends coupled together to form a closed loop. Additional details on implant 10 and the methods of use are disclosed in International PCT Application No. PCT/US2009/055914; International PCT Publication No. WO2009/149407; U.S. Patent Publication Nos. 2010/0023060; 2008/0319487; 2008/0262549; and U.S. Pat. No. 7,458,981; the entire contents of each is incorporated in its entirety herein by reference.

While the exemplary embodiments have been described in some detail for clarity of understanding and by way of example, a number of modifications, changes, and adaptations may be implemented and/or will be obvious to those as skilled in the art. Hence, the scope of the present invention is limited solely by the independent claims.

What is claimed is:

1. A method for improving shear loading capacity of a spinal segment, the spinal segment having a superior vertebra, a superior spinous process on the superior vertebra, an inferior vertebra, an inferior spinous process on the inferior vertebra, or a sacrum, and a facet joint therebetween, said method comprising:
providing a constraint device having an upper portion, a lower portion and a compliance member coupled therebetween, wherein the upper portion comprises a flexible and non-distensible tether, and wherein the lower portion comprises a flexible and non-distensible tether;
coupling the constraint device with the spinal segment, wherein the flexible and non-distensible tether of the upper portion of the constraint device is disposed around a superior surface of the superior spinous process and the flexible and non-distensible tether of the lower portion of the constraint device is disposed around an inferior surface of the inferior spinous process or coupled to the sacrum, and wherein the constraint device provides a force resistant to flexion of the spinal segment without substantially restricting extension; and
adjusting length or tension in the constraint device so as to increase engagement between an upper portion of the facet joint and a lower portion of the facet joint, thereby increasing capacity of the spinal segment to resist shear loading, and
reducing or eliminating further progression of degenerative spondylolisthesis in the spinal segment without fusion thereof.

2. The method of claim 1, wherein the compliance member comprises a coil spring.

3. The method of claim 1, wherein the step of coupling the constraint device is performed minimally invasively.

4. The method of claim 1, wherein the force resistant to flexion resists spreading apart of the superior spinous process relative to an the inferior spinous process.

5. The method of claim 1, wherein the constraint device is coupled with the spinal segment without substantially restricting lateral bending of the spinal segment.

6. The method of claim 1, wherein the constraint device is coupled with the spinal segment without substantially restricting axial rotation of the spinal segment.

7. The method of claim 1, wherein the step of adjusting the length or the tension in the constraint device increases engagement between the upper portion and the lower portion of the facet joint when the spinal segment is in flexion.

8. The method of claim 1, wherein the upper portion of the facet joint comprises an inferior articular process of the superior vertebra and the lower portion of the facet joint comprises a superior articular process of the inferior vertebra.

9. The method of claim 1, wherein increasing the shear-loading capacity of the spinal segment comprises reducing translation of the superior vertebra relative to the inferior vertebra when shear loading is applied to the spinal segment.

10. The method of claim 9, wherein the translation is in an anterior direction.

11. The method of claim 1, wherein increasing the shear-loading capacity of the spinal segment comprises reducing listhesis of the superior vertebra relative to the inferior vertebra when shear loading is applied to the spinal segment.

12. The method of claim 1, wherein the step of adjusting length or tension in the constraint device increases stability of the spinal segment.

13. The method of claim 1, wherein the step of adjusting tension in the constraint device comprises adjusting tension to about 10 to 50 Newtons with the spinal segment in a neutral position.

14. The method of claim 1, wherein the step of adjusting tension in the constraint device comprises adjusting tension to about 10 to 50 Newtons with the patient in a peri-operative implantation position.

15. The method of claim 1, wherein the step of adjusting length in the constraint device comprises adjusting length until the constraint device is taut when the spinal segment is in a neutral position.

16. The method of claim 1, wherein the step of adjusting length or tension in the constraint device comprises adjusting length or tension so that the upper and the lower portions of the facet joint maintain engagement with one another when the spinal segment is in flexion.

17. The method of claim 1, further comprising evaluating the spinal segment.

18. The method of claim 17, wherein the step of evaluating the spinal segment comprises evaluating engagement of the facet joint.

19. The method of claim 17, wherein the step of evaluating the spinal segment comprises evaluating curvature of the spinal segment.

20. The method of claim 17, wherein the step of evaluating the spinal segment comprises evaluating an intervertebral angle of the superior vertebra relative to the inferior vertebra.

21. The method of claim 17, wherein the step of evaluating the spinal segment comprises performing anatomical measurements of the spinal segment or regions adjacent thereto.

22. The method of claim 17, wherein the step of evaluating the spinal segment comprises evaluating stability thereof.

23. The method of claim 17, wherein the step of evaluating the spinal segment comprises fluoroscopically imaging the spinal segment.

24. The method of claim 17, wherein the step of evaluating comprises providing one or more radiographic images of the spinal segment in a plurality of spinal postures.

25. The method of claim 17, wherein the step of evaluating the spinal segment comprises directly visualizing the spinal segment.

26. The method of claim 17, wherein the step of evaluating the spinal segment comprises manually palpating or manipulating the spinal segment.

27. The method of claim 17, wherein the step of evaluating the spinal segment comprises measuring the spinal segment with a measuring instrument.

28. The method of claim 27, wherein the measuring instrument comprises calipers or a ruler.

29. The method of claim 28, wherein the ruler is radiopaque.

30. The method of claim 1, further comprising reducing or eliminating intervertebral translation of the superior vertebra relative to the inferior vertebra.

31. The method of claim 1, further comprising maintaining or improving sagittal alignment of the spinal segment.

32. The method of claim 1, further comprising reducing or eliminating narrowing of a spinal canal or a lateral foramina in the spinal segment caused by translation of the superior vertebra relative to the inferior vertebra.

33. The method of claim 1, further comprising decompressing a portion of the spinal segment thereby relieving pressure on nerves passing therethrough.

34. The method of claim 33, wherein the decompressing step comprises decompressing the spinal segment while preserving at least half of each of the spinous processes in the spinal segment, and without disrupting mechanical integrity of the facet joints.

35. The method of claim 1, further comprising minimizing or preventing disengagement of the upper portion of the facet joint from the lower portion of the facet joint when the spinal segment is in flexion.

36. The method of claim 1, further comprising reducing peak loading on the superior and the inferior vertebrae during flexion of the spinal segment relative to peak loading experienced when the spinal segment is instrumented with pedicle screws or cerclage wiring.

37. The method of claim 1, further comprising reducing peak loading at an interface between the constraint device and the vertebrae during flexion of the spinal segment.

38. A constraint device for improving shear loading capacity of a spinal segment having a superior vertebra with a superior spinous process, an inferior vertebra with an inferior spinous process, and a facet joint therebetween, said device comprising:
- a flexible and non-distensible upper tether structure adapted to be disposed around a superior surface of the superior spinous process on the superior vertebra;
- a flexible and non-distensible lower tether structure adapted to be disposed around an inferior surface of the inferior spinous process on the inferior vertebra or coupled to a sacrum; and
- a compliance member disposed between the upper and the lower tether structures, wherein length or tension in the constraint device is adjustable such that the compliance member provides a force so that the constraint device resists flexion of the spinal segment without substantially restricting extension, and wherein the constraint device is further adapted to increase engagement between an upper portion of the facet joint and a lower portion of the facet joint, thereby increasing capacity of the facet joint to resist shear loading, and
- wherein the length or tension is adjustable such that further progression of degenerative spondylolisthesis in the spinal segment is reduced or eliminated without fusion thereof.

39. The device of claim 38, wherein the upper and the lower tether structures comprise elongate bands.

40. The device of claim 38, further comprising a second compliance member disposed between the upper and the lower tether structures, the compliance members arranged to lie on either side of a spinal segment midline.

41. The device of claim 40, wherein the upper and the lower tether structures are flexible such that neither tether structure transmits complex loading to the compliance members.

42. The device of claim 38, wherein the compliance member comprises a coil spring.

43. The device of claim 38, wherein the constraint device is adapted to be coupled with the spinal segment without substantially restricting lateral bending of the spinal segment.

44. The device of claim 38, wherein the constraint device is adapted to be coupled with the spinal segment without substantially restricting axial rotation of the spinal segment.

* * * * *